(12) United States Patent
Führer et al.

(10) Patent No.: US 7,754,914 B2
(45) Date of Patent: *Jul. 13, 2010

(54) METHOD OF RECOVERING FLUORINATED ACID SURFACTANTS FROM ADSORBENT PARTICLES LOADED THEREWITH

(75) Inventors: Stephan Führer, Kastl (DE); Klaus Hintzer, Kastl (DE); Gernot Löhr, Burgkirchen (DE); Egon Obermaier, Taubenbach (DE); Werner Schwertfeger, Altoetting (DE)

(73) Assignee: 3M Innovative Properties Company, St. Paul, MN (US)

( * ) Notice: Subject to any disclaimer, the term of this patent is extended or adjusted under 35 U.S.C. 154(b) by 933 days.

This patent is subject to a terminal disclaimer.

(21) Appl. No.: 11/036,432

(22) Filed: Jan. 14, 2005

(65) Prior Publication Data

US 2005/0177000 A1    Aug. 11, 2005

(30) Foreign Application Priority Data

Feb. 5, 2004    (EP)    .................... 04075377

(51) Int. Cl.
  C07C 69/63    (2006.01)
  C07C 53/21    (2006.01)
(52) U.S. Cl. ...................... 560/227; 562/605
(58) Field of Classification Search ................. 560/227; 562/605
  See application file for complete search history.

(56) References Cited

U.S. PATENT DOCUMENTS

| | | | |
|---|---|---|---|
| 3,882,153 A | | 5/1975 | Seki et al. |
| 4,005,137 A | | 1/1977 | Rudolph et al. |
| 4,282,162 A | | 8/1981 | Kuhls |
| 4,391,940 A | * | 7/1983 | Kuhls et al. ............ 524/458 |
| 4,396,266 A | | 8/1983 | Goto |
| 4,446,109 A | | 5/1984 | Bakke |
| 5,229,480 A | | 7/1993 | Uschold |
| 5,442,097 A | * | 8/1995 | Obermeier et al. ......... 560/227 |
| 5,688,884 A | | 11/1997 | Baker et al. |
| 5,700,859 A | | 12/1997 | Ogura et al. |
| 5,763,552 A | | 6/1998 | Feiring et al. |
| 5,804,650 A | | 9/1998 | Tsuda et al. |
| 5,895,799 A | | 4/1999 | Wu et al. |
| 6,025,307 A | | 2/2000 | Chittofrati et al. |
| 6,103,843 A | | 8/2000 | Abusleme et al. |
| 6,126,849 A | | 10/2000 | Yamana et al. |
| 6,436,244 B1 | | 8/2002 | Fuhrer et al. |
| 6,518,442 B1 | * | 2/2003 | Felix et al. ............ 554/177 |
| 6,613,941 B1 | | 9/2003 | Felix et al. |
| 6,642,307 B1 | | 11/2003 | Sogabe et al. |
| 6,833,403 B1 | | 12/2004 | Blädel et al. |
| 7,018,541 B2 | | 3/2006 | Hintzer et al. |
| 2002/0151748 A1 | | 10/2002 | Jones et al. |

FOREIGN PATENT DOCUMENTS

| | | |
|---|---|---|
| EP | 0 194 691 A2 | 9/1986 |
| EP | 0 194 692 A2 | 9/1986 |
| EP | 0 712 882 A1 | 5/1996 |
| EP | 0 752 432 A2 | 1/1997 |
| EP | 0 816 397 A1 | 1/1998 |
| EP | 1 059 342 A1 | 12/2000 |
| WO | WO 00/71590 A1 | 11/2000 |

OTHER PUBLICATIONS

*Encyclopedia of Chemical Technology*, Kirk-Othmer, John Wiley & Sons, 3rd Edition, vol. 13, "Ion Exchange", 1978, p. 687.
*Encyclopedia of Polymer Science and Engineering*, John Wiley & Sons, vol. 8, "Ion-Exchange Polymers", 1985, p. 347.
Database WPI; Section Ch, Week 200355; Derwent Publications ltd., London, GB; AN 2003-350439; XP002288163, and KR 381 453 B (Ashin Technology Co. Ltd), May 1, 2003—Abstract.
Database CHEMABS 'Online'; Chemical Abstracts Service, Columbus, Ohio, US; Bystrov, G.A. et al; "Final treatment of wastewaters on activated carbon"; XP002288162, retieved from STN Database accession No. 113:11571, Abstract, *Plasticheskie Massy*, (4), 75-8 CODEN;PLMSAI; ISSN: 0554-2901, (1990).
Bystrov, G. A., et al., "Carbon Adsorption Post-Treatment of the Waste Waters Containing Perfluoroacids," *Plasticheskie Massy* No. 4 (1990) p. 75-80.

* cited by examiner

*Primary Examiner*—Porfirio Nazario Gonzalez
(74) *Attorney, Agent, or Firm*—Julie A. Lapos-Kuchar; Brian E. Szymanski

(57) ABSTRACT

The present invention provides a method of recovering a fluorinated acid surfactant or salt thereof from adsorbent particles to which said fluorinated acid surfactant has been adsorbed. The method comprises mixing adsorbent particles having adsorbed fluorinated acid surfactant or salt thereof with an alcohol and optionally an acid. The mixture is generally heated to cause esterification of the fluorinated acid surfactant or salt thereof with the alcohol so as to form an ester derivative of the fluorinated acid surfactant, distilling the mixture to form a distillate comprising the ester derivative, separating the ester derivative from the distillate and optionally feeding the remainder of the distillate back into the mixture.

9 Claims, No Drawings

METHOD OF RECOVERING FLUORINATED ACID SURFACTANTS FROM ADSORBENT PARTICLES LOADED THEREWITH

This application claims priority from European Patent Application Serial No. 04075377.4, filed Feb. 5, 2004.

1. FIELD OF THE INVENTION

The present invention relates to the recovering fluorinated acid surfactants in their acid or salt form from adsorbent particles that have been loaded with the fluorinated acid surfactant or salt thereof.

2. BACKGROUND OF THE INVENTION

Fluoropolymers, i.e. polymers having a fluorinated backbone, have been long known and have been used in a variety of applications because of several desirable properties such as heat resistance, chemical resistance, weatherability, UV-stability etc. The various fluoropolymers are for example described in "Modern Fluoropolymers", edited by John Scheirs, Wiley Science 1997. The fluoropolymers may have a partially fluorinated backbone, generally at least 40% by weight fluorinated, or a fully fluorinated backbone. Particular examples of fluoropolymers include polytetrafluoroethylene (PTFE), copolymers of tetrafluoroethylene (TFE) and hexafluoropropylene (HFP) (FEP polymers), perfluoroalkoxy copolymers (PFA), ethylene-tetrafluoroethylene (ETFE) copolymers, terpolymers of tetrafluoroethylene, hexafluoropropylene and vinylidene fluoride (THV) and polyvinylidene fluoride polymers (PVDF).

A frequently used method for producing fluoropolymers involves aqueous emulsion polymerization of one or more fluorinated monomers resulting in an aqueous dispersion of the fluoropolymer. The aqueous emulsion polymerization of fluorinated monomers generally involves the use of a fluorinated surfactant. Frequently used fluorinated surfactants include perfluorooctanoic acids and salts thereof, in particular ammonium perfluorooctanoic acid. Further fluorinated surfactants used include perfluoropolyether surfactants such as disclosed in EP 1059342, EP 712882, EP 752432, EP 816397, U.S. Pat. No. 6,025,307, 6,103,843 and 6,126,849. Still further surfactants that have been used are disclosed in U.S. Pat. No. 5,229,480, 5,763,552, 5,688,884, 5,700,859, 5,804,650, 5,895,799, WO 00/22002 and WO 00/71590.

Perfluorocarboxylic acids (PFCA) are the preferred emulsifiers for making fluorinated polymers, e.g. perfluorinated polymers like PTFE, FEP, PFA, perfluorinated elastomers, and others. Especially perfluorooctanoic acid (PFOA) in form of its salts (e.g. ammonium salt, APFO) is widely used. But, APFO and other fluorinated surfactants, in particular perfluorinated surfactants have raised environmental concerns. Another important aspect is the fact that these surfactants are expensive materials and any losses thereof from the production process should be minimized. Until now, these emulsifiers, especially APFO are indispensable because they do not display chain transfer properties. So PFOA or APFO respectively are just a prominent example for a whole class of fluorinated surfactants, in particular fluorinated surfactants with carboxylic acid groups.

The fluoropolymers may be used to coat substrates to provide desirable properties thereto such as for example chemical resistance, weatherability, water- and oil repellency etc. For example aqueous dispersions of fluoropolymer may be used to coat kitchen ware, to impregnate fabric or textile e.g. glass fabric, to coat paper or polymeric substrates. For sake of economy and convenience, the fluoropolymer dispersions will typically have between 35% by weight and 70% by weight of fluoropolymer solids, which is typically attained using an upconcentration process. Alternatively, for some applications, the fluoropolymers are provided in granular or powder form. To obtain fluoropolymer granulate or powder, the fluoropolymer is typically coagulated and the resulting coagulate may be washed with water one or more times to obtain a desired level of purity.

During the production of fluoropolymers to their final commercial form, waste water streams are created that contain fluorinated surfactant. For example, waste water streams may result from upconcentration of the dispersion, cleaning of the polymerization vessel and equipment, coagulation of the dispersion and washing to obtain fluoropolymer granulate or powder. Additionally, waste water containing fluorinated surfactant may result during application of the fluoropolymers. Frequently, the waste water streams not only contain fluorinated surfactant but also other components such as a small amount of fluoropolymer particles.

Several methods for the removal of PFCAs from aqueous media are known. For example, a method employing reverse osmosis is described in WO 02/139593. A combined process of extracting PFCA from aqueous solutions at low pH levels using chlorinated hydrocarbons and contacting the organic layer with alumina to recover the PFCA is described in EP 194692 and EP 194691. DE 2407834 discloses the use of silica gel to separate PFCAs from aqueous solutions.

Treatment of PFCA contaminated water can be done by applying reverse osmosis followed by an active carbon bed absorption including the regeneration thereof with ethanol as described by G. A. Bystrov et al, Plasticheskie Massy, (1990), (4), 75-8 (CA 113, 11571). As reported by the Russian Authors, the PFCA contaminated water (40-4000 mg of PFCA per liter) is purified by reverse osmosis in an initial step, resulting in water containing less than 20 mg per liter of PFCA. This level can be further reduced in an additional purification step using an active carbon bed. At break through of PFCA, the loaded active carbon bed is regenerated. Although several different methods were tried, the Soxhlet extraction with solvents, especially a ethanol-water mixture, showed the best results. But even in this case only 65% of the absorbed PFCA could be removed. The thus regenerated active carbon showed a decrease of activity in the range of 25-40%. Based on this result it is stated that the active carbon can be reused only 2-3 times before it has to be discarded.

It will generally be desired to recover the fluorinated surfactant from the adsorbent particles such that the expensive fluorinated surfactant can be reused in a polymerization process and the adsorbent particles can be reused in a purification of waste water. While the efficiency of the adsorbent particles may decrease after reuse, it would be desirable to regenerate the adsorbent particles such that they can be reused more frequently before they have to be discarded because of unacceptable low efficiency levels.

A still further method concerns the use of an anion exchange resin to recover PFCAs from fluoropolymer particle containing waste water. Such method has been disclosed in WO 99/62858 and WO 99/62830. According to WO 99/62858, the fluoropolymer particles are removed from the waste water before contacting the waste water with the anion exchange resin.

According to WO 99/62830, a non-ionic surfactant is added to the waste water before contacting the latter with the exchange resin. Thus, in this method the PFCA is bonded to the exchange resin via an anion exchange mechanism but also physical adsorption to the resin particles is believed to take place in the removal process. According to the teaching of these WO applications, the fluorinated surfactant can be recovered from the anion exchange resin by eluting the anion exchange resin with an appropriate regeneration fluid releasing the fluorinated surfactant from the anion exchange resin. A disadvantage of the recovery method for the fluorinated surfactant from an anion exchange resin is that large amounts of regeneration are generally required which adds to the cost of regeneration and is further inconvenient.

It would thus be desirable to find a further process for the recovery of fluorinated acid surfactants, from adsorbent particles loaded with the fluorinated surfactant. Desirably such process is efficient, use minimal amounts of regeneration fluids, preferably is convenient and preferably results in regenerated adsorbent particles that can be reused multiple times.

3. SUMMARY OF THE INVENTION

The present invention provides a method of recovering a fluorinated acid surfactant or salt thereof from adsorbent particles to which said fluorinated acid surfactant has been adsorbed. The method comprises mixing adsorbent particles having adsorbed fluorinated acid surfactant or salt thereof with an alcohol and optionally an acid. The mixture is generally heated to cause esterification of the fluorinated acid surfactant or salt thereof with the alcohol so as to form an ester derivative of the fluorinated acid surfactant. The method further includes distilling the mixture to form a distillate comprising the ester derivative, separating the ester derivative from the distillate and optionally feeding the remainder of the distillate back into the mixture.

By the term 'fluorinated acid surfactant' in connection with this invention is meant a surfactant having a fluorinated hydrocarbon group and an acid group. For sake of convenience, the term will be used to indicate the acid form as well as the salt form in the remainder of the description of the invention.

By the term 'absorbent particles' in connection with the present invention is meant particles that are capable of physically adsorbing the fluorinated surfactant by whatever mechanism of physical adsorption including but not limited to ionic interactions causing physical adsorption. Accordingly, the term 'adsorbent particles' include ion exchange resins, which typically bind fluorinated surfactants having ionic groups as a result of an ion exchange process although the adsorption to the exchange resin may also occur by a physical adsorption process other than the ion exchange process.

4. DETAILED DESCRIPTION OF THE INVENTION

Adsorbent particles

Suitable adsorbent particles include carbon black, silica gel, clays and zeolites. Conveniently used are carbon black particles. The shape of the adsorbent particles is not particularly critical. For example, the adsorbent particles may have a plate shape, can be spherical, cylindrical or they can be rods. Also, adsorbent particles having a variety of different shapes may be used as a mixture. The size of the adsorbent particles is typically between 0.05 mm and 20 mm, generally between 0.1 and 10 mm. A practical range is between 0.5 and 5 mm. The adsorbent particles typically adsorb the fluorinated acid surfactant on their surface and it will thus generally be preferred to optimize the specific surface area of the particles, i.e. the amount of surface per unit of weight. Typically, the specific surface area of the adsorbent particles will be between 10 and 5000 $m^2/g$, generally between 100 and 3000 $m^2/g$ with a practical range being from 300 to 2000 $m^2/g$.

Additionally, anion exchange resin particles can be used as adsorbent particles. Examples of anion exchange resin that can be used to adsorb a fluorinated acid surfactant on to which the process of the invention may be applied include strong, medium as well as weak basic anion exchange resins. The terms strong, medium strong and weak basic anion exchange resin are defined in "Encyclopedia of Polymer Science and Engineering", John Wiley & Sons, 1985, Volume 8, page 347 and "Kirk-Othmer", John Wiley & Sons, 3$^{rd}$ edition, Volume 13, page 687. Strong basic anion exchange resin typically contains quaternary ammonium groups, medium strong resins usually have tertiary amine groups and weak basic resins usually have secondary amines as the anion exchange functions. Examples of anion exchange resins that are commercially available for use in this invention include AMBERLITE® IRA402, AMBERJET® 4200, AMBERLITE® IRA-67 and AMBERLITE® IRA-92 all available from Rohm & Haas, PUROLITE® A845 (Purolite GmbH) and LEWATIT® MP-500 (Bayer AG).

Surprisingly, the anion exchange resin particles are not negatively affected in the recovery process of this invention and can be re-used in adsorbing fluorinated acid surfactant from for example waste water.

The adsorbent particles may be loaded to any degree with the fluorinated acid surfactant, but generally the process will be more efficient the higher the loading degree of the adsorbent particles is. Typically, the adsorbent particles will be loaded with fluorinated acid surfactant in an amount of 5 to 100%, generally 30 to 95% of the nominal loading capacity of the adsorbent particles. The nominal loading capacity of adsorbent particles may be determined by loading 'fresh' adsorbent particles with a 0.1% aqueous solution of the fluorinated acid surfactant until a break through is observed. A break-through is defined as the point at which at least 10% of the amount of fluorinated surfactant contained in the aqueous solution is still present after contacting the aqueous solution with the adsorbent particles.

The loaded adsorbent particles may result from a variety of recovery processes. For example, the loaded adsorbent particles may come from the removal of fluorinated acid surfactant from waste water streams generated in the manufacturing, handling and processing of fluoropolymers. Alternatively, the adsorbent particles may have been loaded with fluorinated acid surfactant in a process of removing fluorinated surfactant from fluoropolymer dispersions as is disclosed in e.g. WO 00/35971 or from the removal of fluorinated surfactant from permeates resulting from ultrafiltration as disclosed in U.S. Pat. No. 4,396,266.

Fluorinated Acid Surfactant

The fluorinated acid surfactant is a fluorinated hydrocarbon surfactant having at least one acid group. Generally, the surfactant will be a perfluorinated hydrocarbon surfactant. Examples of acid groups included in the surfactant include carboxylic acid groups, sulphonic acid groups and phosphoric acid groups. The method of the present invention is particularly suitable to recover (per)fluorinated aliphatic acid surfactants or salts thereof from adsorbent particles to which the surfactants have been adsorbed. The method of the present invention can conveniently be used to recover fluorinated surfactants according to the following formula:

$$Q-R_f-Z-M^a \qquad (I)$$

wherein Q represents hydrogen, Cl or F whereby Q may be present in terminal position or not; $R_f$ represents a linear or branched perfluorinated alkylene having 4 to 15 carbon atoms; Z represents $COO^-$, $M^a$ represents a cation including $H^+$, an alkali metal ion or an ammonium ion. Representative examples of fluorinated surfactants according to above formula (I) are perfluoroalkanoic acids and salts thereof such as perfluorooctanoic acid and its salts in particular ammonium salts.

Regeneration Fluid

In accordance with the present invention, to recover the fluorinated acid surfactant from the adsorbent particles, the adsorbent particles loaded with the fluorinated acid surfactant are mixed with a regeneration fluid comprising an alcohol, optionally an acid and generally also water. The regeneration fluid may be prepared in advance and mixed with the adsorbent particles or the individual components may be mixed separately with the adsorbent particles. Although the order of addition will not be particularly critical, it will generally be preferred to add the acid as the last component. The addition of an acid is not mandatory as the fluorinated acid surfactant may autocatalyse the esterification with the alcohol. Nevertheless, typically an acid is added in the regeneration fluid.

Suitable alcohols that may be used include in particular lower aliphatic alcohols having 1 to 5 carbon atoms such as methanol, ethanol and propanol. However aromatic alcohols may be used as well. Additionally, the alcohol may be added under the form of a precursor of the alcohol. Such a precursor should however form an alcohol under the conditions used to cause the esterification. Suitable precursors of the alcohol may include compounds such as ketals that readily form a corresponding alcohol under the acidic conditions existing in the regeneration fluid or mixture thereof with the adsorbent particles. The acid used with the regeneration fluid is preferably an inorganic acid but the use of organic acids is not excluded. Also, the acid is preferably a strong acid such as for example sulphuric acid, hydrochloric acid, phosphoric acid or nitric acid. The amount and nature of the acid used is typically such that a pH of less than 4, preferably not more than 3 and more preferably not more than 2 is attained in the mixture of regeneration fluid and adsorbent particles.

The total amount of regeneration fluid and its composition is typically determined on basis of the amount of loaded adsorbent particles to be regenerated and the actual loading of the particles. Generally, the regeneration fluid should contain the alcohol in a stoichiometric amount or stoichiometric excess of the amount of fluorinated acid surfactant loaded on the adsorbent particles offered for regeneration. If this data is not available, one should generally apply a large excess of the regeneration liquid. This does not adversely affect the regeneration process but has the disadvantage that a non-optimal amount of regeneration liquid is used. The excess regeneration liquid can easily be drained from the regenerated adsorbent particles after the regeneration process is finished. The drained liquid can be weighed and analyzed to determine the actual amount and composition of the drained regeneration liquid. The composition and amount of the drained regeneration liquid can then be adjusted by adding appropriate amounts of its components so that the drained regeneration liquid may be re-used. Reuse of the regeneration liquid will create less waste, is environmentally friendly, and reduces the costs.

The volume ratio of regeneration fluid to adsorbent particles is preferably at least 2 although lower volume ratios may be used as well. However, lower volume ratios may cause damage to the adsorbent particles because of stresses generated at lower volume ratios. Higher volume ratios can be practiced but too large volume ratios will generally be uneconomical. Typically the volume ratio will be between 2 and 4.

Recovery Process

In accordance with an embodiment of the process of the invention, the mixture of adsorbent particles and regeneration fluid is typically heated to cause esterification of the fluorinated acid surfactant and the mixture is distilled. In one embodiment, heating and distilling may be carried out simultaneously, i.e. immediately after mixing the adsorbent particles and the regeneration fluid, the mixture is being distilled. Alternatively, the mixture may be heated for some time, generally to the boiling point, until distillation is started. Also, esterification may be caused without heating the mixture, for example by stirring the mixture at ambient temperature for some time. However, it will generally be more efficient to heat the mixture to cause esterification.

The recovery process can be carried out at ambient pressure, positive pressure, and under reduced pressure. Typically, the process is carried out at a pressure between 0.1 and 2 atm, conveniently at ambient pressure, i.e. about 1 atm. The mixture will typically be heated to the boiling point of the mixture but lower temperatures can be used as well for converting the fluorinated acid surfactant in its ester derivative. Typically, the process is carried out at a temperature of between 30 and 100° C., commonly between 50 and 85° C.

The mixture containing the adsorbent particles and ester derivative of the fluorinated acid surfactant is distilled. The distillate that forms contains the ester derivative. With a sufficient amount of water present in the distillate the ester derivative will generally easily separate out as a separate phase from the remainder of the distillate. The distillate will typically contain sufficient water if a substantial amount of water is contained in the regeneration fluid. Alternatively, water may be added to distillate to cause separation. Typically, the ester derivative will form the lower phase. Thus, the ester derivative can be easily separated from the distillate and the remainder of the distillate may be re-introduced into the mixture being distilled. Such an embodiment thus allows for convenient recovery of the fluorinated surfactant with a minimal amount of regeneration fluid being needed. Also, with the latter continuous re-use of the regeneration fluid, the distillation can be commenced readily immediately after mixing the regeneration fluid and the adsorbent particles.

It has been found that the recovery process is highly effective and allows for re-use of the adsorbent particles multiple times, i.e., they can be regenerated several times before their efficiency drops below an uneconomical level at which point the adsorbent particles need to be disposed of. Furthermore, the process is highly efficient in removing fluorinated surfactant from the adsorbent particles such that even when the adsorbent particles need to be disposed of, because of their lost efficiency, the remaining levels of fluorinated surfactant in the adsorbent particles is very low. Also, any other substances that may be adsorbed on the adsorbent particles in addition to the fluorinated acid surfactant, such as fluoropolymer particles, do not generally interfere with the recovery of the fluorinated acid surfactant and regeneration of the adsorbent particles. It was found that the recovery process is capable of releasing also these fluoropolymer particles to a large extent from the adsorbent particles.

As will be appreciated by one skilled in the art, upon distillation, the process yields the ester derivative of fluorinated acid surfactant. This ester derivative can be converted back into the corresponding fluorinated acid surfactant or salt thereof by hydrolysing the ester derivative as is known to those skilled in the art. The thus obtained fluorinated acid surfactant or salt thereof is of a sufficiently high quality so that it can be reused in the polymerization of fluorinated monomers to make fluoropolymers.

The invention will now be further described with reference to the following examples without however the intention to limit the invention thereto.

EXAMPLES

Examples 1 to 3

Aqueous ammonium perfluorooctanoate (APFO) was used to load active carbon, which were used as the adsorbent particles. Residual free APFO was removed by washing once with water prior to the regeneration step. Samples of the aqueous phase were analyzed for material balance.

Activated charcoal was used in the tests. The activated carbon was received from Merck in granulated form with a particle size of 1.5 mm.

Recovery Process

In the following examples, the recovery process used was as follows:

120 g (230 ml) of dry active carbon (wet weight after treatment with water: 277 g) and aqueous ammonium perfluorooctanoate (concentration 25000 ppm APFO) are agitated at room temperature to conduct the loading process. Although the mixture looks turbid after the loading process only a minor amount of fines was detected. The loaded active carbon was washed once with water and transferred to a distillation apparatus consisting of a flask equipped with a mechanical stirrer, thermometer, vapor line, and a condenser. The regeneration liquid consisting of methanol, water and sulfuric acid was added. The mixture was heated at the desired pressure until distillation started. The condensed vapor separated in two liquid phases. The lower phase was removed while the upper phase was returned to the distillation flask. More than 90% of the lower phases are separated in the first few hours. The distillation was stopped as soon as no increase of the lower phase is observed. The lower phase of the distillate consisted of methyl perfluorooctanoate. Again, only a negligible amount of fines was detected.

Example 1

34.4 g APFO was loaded on the carbon in the initial cycle. This represents a loading of 28.6 weight % based on the dry active carbon. Regeneration resulted in 30.8 g of PFOA methyl ester. This corresponds to a recovery of 89.5% of the loaded APFO.

Example 2

The regenerated active carbon of example 1 was washed with water (wet weight: 289 g). In the second loading 35.5 g of APFO was adsorbed. Regeneration of the loaded carbon resulted in 34.5 g of PFOA methyl ester. This corresponds to a recovery of 97.2% of the loaded APFO.

Example 3

The regeneration was essentially carried out like the previous procedure using the regenerated active carbon of example 2. 35.6 g of APFO were adsorbed. Regeneration yielded 34 g of PFOA methyl ester (recovery of 95.5%).

Example 4

Two glass columns (diameter 4.5 cm) were loaded with dry active carbon. The first column contained 201 g and the second column 205 g active carbon. The volume of each bed is ca. 400 ml. The columns were connected and water was pumped through until all gas was removed. An aqueous solution containing 1200 ppm APFO and 30 ppm Genapol™ X080 (non-ionic surfactant available from Clariant GmbH) at a pH of 5.9 was passed over the columns from the bottom to the top. The flow rate was adjusted to one bed volume per hour. Samples were taken and analyzed for residual APFO.

The following APFO content was detected in the effluent of the first column (see table). As expected no APFO was found in the effluent of the second column.

| APFO loaded, g | PFOA in effluent |
|---|---|
| 6.6 g | <1 ppm |
| 16.6 g | 4 ppm |
| 22.5 g | 5 ppm |
| 38.3 g | 6 ppm |
| 43.5 g | 7 ppm |
| 46.8 g | 23 ppm |
| 51.3 g | 100 ppm |
| 55.6 g | 112 ppm |

The columns were washed with 5 liters of de-ionized water. The content of the first column was transferred to a flask and the regeneration was carried out as described above. 50.6 g of PFOA methyl ester were received. This corresponds to 91% of the loaded APFO.

Examples 5-18

Aqueous ammonium perfluorooctanoate (APFO) was used to load the anion exchange resins identified below. If a fully loaded anion exchange resin was desired, excess APFO, based on the capacity of the anion exchange resin as disclosed by the manufacturer was used. Residual free APFO was removed by washing once with water. The following anion exchange resins were used:

A. AMBERLITE™ IRA 402 Cl (Rohm & Haas, chloride form)≧1.3 eq/liter, strong basic B. AMBERLITE™ IRA 92 (Rohm & Haas)≧1.6 eq/liter, weak basic C. AMBERLYST™ A 26 OH (Rohm & Haas, hydroxide form)≧0.8 eq/liter, strong basic General Description of the Loading and Regeneration Process Wet anion exchange resin and aqueous APFO were agitated at room temperature to conduct the loading process. APFO was added until the anion exchange resin was saturated with perfluorooctanoic acid (PFOA). The saturated anion exchange resin was washed once with water and transferred to a distillation apparatus consisting of a flask equipped with a mechanical stirrer, thermometer, vapor line, and a condenser. The regeneration liquid consisting of methanol, water and sulfuric acid was added. The mixture was heated at the desired pressure until distillation starts. The condensed vapor separated in two liquid phases. The lower phase was removed while the upper phase was sent back to the distillation flask. More than 90% of the lower phase was separated in the first few hours. The distillation was finished as soon as no increase of the lower phase was observed. The lower phase of the distillate consisted of methyl perfluorooctanoate (Me-PFOA). The anion exchange resin was separated from the remaining mixture in the flask by filtration or decantation. The liquid could be reused for the next regeneration batch, e.g. after addition of the consumed methanol and sulfuric acid. After washing the anion exchange resin with water, it could be re-used for the next loading.

Examples 5-8

| Ex. | Resin type and amount | Degree of loading with APFO | Regeneration mixture | Distillation parameters | Amount of lower phase (Me-PFOA), g |
|---|---|---|---|---|---|
| 5 | A Cl Form 250 ml | Exhausted and washed with water | H2SO4, 100 g Methanol, 300 g Water, 100 g | Pressure: ambient Reboiler temp. 75° C. Dist. time 12 h | 141 g |
| 6 | From Ex 5 sulfate form | Exhausted and washed with water | H2SO4, 100 g Methanol, 600 g Water, 100 g | Pressure: ambient Reboiler temp. 73° C. Dist. time 10 h | 144 g |
| 7 | From Ex 6 sulfate form | Exhausted and washed with water | H2SO4, 100 g Methanol, 300 g Water, 100 g | Pressure: ambient Reboiler temp. 76° C. Dist. time 10 h | 138 g |
| 8 | From Ex 7 sulfate form | Exhausted and washed with water | H2SO4, 100 g Methanol, 300 g Water, 100 g | Pressure: ambient Reboiler temp. 73° C. Dist. time 10 h | 147 g |

Examples 9-18

| Ex. | Resin type and amount | Degree of loading with APFO | Regeneration mixture | Distillation parameters | Amount of lower phase (Me PFOA), g |
|---|---|---|---|---|---|
| 9 | C OH form 250 ml | Exhausted and washed with water | H2SO4, 100 g Methanol, 300 g Water, 100 g | Pressure: ambient Reboiler temp. 78° C. Dist. time 5 h | 101 g |
| 10 | From Ex. 9 sulfate form | Exhausted and washed with water | H2SO4, 100 g Methanol, 300 g Water, 100 g | Pressure: ambient Reboiler temp. 78° C. Dist. time 10 h | 103 g |
| 11 | From Ex. 10 sulfate form | Exhausted and washed with water | H2SO4, 100 g Methanol, 300 g Water, 100 g | Pressure: ambient Reboiler temp. 78° C. Dist. time 10 h | 103 g |
| 12 | C OH form 400 ml | Loaded with 151 g APFO | H2SO4, 200 g Methanol, 600 g Water, 200 g | Pressure: ambient Reboiler temp. 77° C. Dist. time 5 h | 147 g |
| 13 | B 300 ml | Loaded with 112 g APFO | H2SO4, 150 g Methanol, 450 g Water, 150 g | Pressure: ambient Reboiler temp. 77° C. Dist. time 14 h | 110 g |
| 14 | C OH form 250 ml | Loaded with 101 g APFO | H2SO4, 100 g Methanol, 300 g Water, 100 g | Pressure: ambient Reboiler temp. 78° C. Dist. time 7 h | 101 g |
| 15 | From Ex 14 sulfate form | Loaded with 108 g APFO | H2SO4, 100 g Methanol, 300 g Water, 100 g | Pressure: ambient Reboiler temp. 78° C. Dist. time 11 h | 102 g |

-continued

| Ex. | Resin type and amount | Degree of loading with APFO | Regeneration mixture | Distillation parameters | Amount of lower phase (Me PFOA), g |
|---|---|---|---|---|---|
| 16 | C OH form 400 ml | Loaded with 151 g APFO | H2S04, 200 g Methanol, 600 g Water, 200 g | Pressure: ambient Reboiler temp. 77° C. Dist. time 8 h | 149 g |
| 17 | From Ex 16 sulfate form | Loaded with 151 g APFO | From batch 15 Analysis: H2SO4 11.5 wt % Methanol 44.3 wt % | Pressure: ambient Reboiler temp. 80° C. Dist. time 13 h | 148 g |
| 18 | From Ex 17 sulfate form | Loaded with 151 g APFO | From batch 16 803 g plus H2SO4, 100 g Methanol, 300 g | Pressure: ambient Reboiler temp. 79° C. Dist. time 13 h | 148 g |

What is claimed is:

1. Method of recovering a fluorinated acid surfactant or salt thereof from adsorbent particles to which said fluorinated acid surfactant has been adsorbed, said method comprising mixing adsorbent particles having adsorbed fluorinated acid surfactant or salt thereof with an alcohol and optionally an acid, causing esterification of said fluorinated acid surfactant or salt thereof with said alcohol so as to form an ester derivative of said fluorinated acid surfactant, distilling the mixture to form a distillate comprising the ester derivative, separating the ester derivative from the distillate and optionally feeding the remainder of the distillate back into said mixture, wherein said method does not include elution with water of the adsorbed fluorinated acid surfactant from the adsorbent particles before distilling the mixture such that the adsorbed particles are included in the mixture being distilled.

2. Method according to claim 1 wherein said adsorbent particles comprise carbon black or an anion exchange resin.

3. Method according to claim 1 wherein said fluorinated acid surfactant comprises a perfluorinated aliphatic acid or salt thereof.

4. Method according to claim 1 wherein said alcohol is an aliphatic alcohol having between 1 and 5 carbon atoms.

5. Method according to claim 1 wherein the amount and nature of said acid is selected such that the mixture has a pH of 2 or less.

6. Method according to claim 5, wherein said acid is an inorganic acid.

7. Method according to claim 1 wherein said esterification is caused by heating said mixture.

8. Method according to claim 1 wherein said esterification is caused in the presence of water.

9. Method according to claim 1 further comprising converting said ester derivative into the corresponding fluorinated acid surfactant or a salt thereof.

* * * * *